United States Patent [19]

Chermann et al.

[11] Patent Number: 4,956,292

[45] Date of Patent: Sep. 11, 1990

[54] VIRAL STRAIN ISOLATED FROM CEREBROSPINAL FLUID OF AN HIV SEROPOSITIVE MAN HAVING ACUTE AND REGRESSIVE ENCEPHALOPATHY AND USE OF THE STRAIN IN AN IMMUNOASSAY

[75] Inventors: Jean-Claude Chermann, Elancourt; Blandine Rouquette; Francoise Rey, both of Paris; Francoise Barre-Sinoussi, Issy Les Moulineaux, all of France

[73] Assignee: Institut Pasteur, Paris, France

[21] Appl. No.: 114,021

[22] Filed: Oct. 29, 1987

[51] Int. Cl.$^5$ .................. C12N 7/00; C12N 15/00
[52] U.S. Cl. .................. 435/235; 435/172.3; 435/172.1; 435/5; 435/948

[58] Field of Search ............ 435/235, 5, 172.1, 172.3, 435/948

[56] References Cited

PUBLICATIONS

Lasky, et al. *Cell,* 50:975–985, 1987.

Primary Examiner—Robin Teskin
Assistant Examiner—Beth A. Burrous
Attorney, Agent, or Firm—Finnegan, Henderson, Farabow, Garrett & Dunner

[57] ABSTRACT

A new viral strain from the cerebrospinal fluid of an HIV seropositive man is identified. The new strain, products derived from the new strain, a diagnostic method for detecting antibodies to the new strain in biological fluids, and a diagnostic kit for carrying out the method are described.

1 Claim, 1 Drawing Sheet

VIRAL STRAIN ISOLATED FROM CEREBROSPINAL FLUID OF AN HIV SEROPOSITIVE MAN HAVING ACUTE AND REGRESSIVE ENCEPHALOPATHY AND USE OF THE STRAIN IN AN IMMUNOASSAY

BACKGROUND OF THE INVENTION

This invention relates to a new strain of Human Immunodeficiency Virus (HIV), which is the major etiological agent of Acquired Immune Deficiency Syndrome (AIDS). More particularly, this invention relates to the new strain, products derived from the new strain, a diagnostic method for detecting antibodies to the strain in biological fluids, and to a diagnostic kit for carrying out the method.

Acquired Immune Deficiency Syndrome (AIDS) was first recognized as a unique clinical syndrome consisting of opportunistic infection with or without neoplasia associated with unexplained immunodeficiency. It was eventually discovered that AIDS was caused by a family of viruses, which are now identified as Human Immunodeficiency Virus (HIV).

The clinical spectrum of disease caused by HIV is not limited to immunosuppression. Neurological manifestations are also observed, and these manifestations are not restricted to infections or primary lymphoma; numerous recent reports suggest a neurotropism of HIV. Symptoms and signs of central nervous system involvement may be associated to seroconversion, ARC and AIDS, or may be the sole manifestation of HIV infection. However, there is no description of acute and regressive central nervous system involvement during the course of chronic systemic HIV-1 infection.

More particularly, several neurological disorders have been related to Human Immunodeficiency Virus (HIV). Acute encephalopathy and aseptic meningitis have been associated to seroconversion (1), and vacuolar myelopathy and AIDS dementia complex to the chronic infection (2-3). AIDS dementia complex may appear as one of the first major manifestations of HIV infection (4). These findings and the isolation of HIV from cerebrospinal fluid and neural tissues (5) suggest direct or indirect central nervous system (CNS) infection by HIV that may occur early in the course of systemic virus infection.

There exists a need in the art for information on variants of HIV. More particularly, there exists a need in the art to investigate the underlying mechanisms of HIV. Indeed, variations in HIV are likely to be associated with important biological functions, and their delineation would be a step towards understanding the molecular mechanisms of viral pathogenicity. More importantly, identification and isolation of retroviral variants must first be achieved.

SUMMARY OF THE INVENTION

This invention aids in fulfilling these needs in the art. This invention involves a case of a seropositive patient without immunodeficiency and with central nervous system involvement that resolved quickly without treatment. Search for a viral, bacterial or fungal etiology was unsuccessful using serology and culture from blood, urine and throat. HIV-1 was isolated from cerebrospinal fluid only when the patient was presenting neurological disorder, but was not obtained when the symptoms disappeared. Virus isolation from peripheral blood lymphocytes was always unsuccessful, and the virus isolated does not grow in normal human T4 lymphocytes.

This invention provides a human retrovirus, wherein the retrovirus is a retroviral variant of Human Immunodeficiency Virus (HIV). Specifically, the retrovirus of the invention:

(a) is immunologically recognized by human serum containing antibody to HIV-1, wherein the serum is from a patient without severe immunodeficiency or clinical features of lymphadenopathy syndrome, malignancy or opportunistic infections associated with AIDS, LAS or ARC;

(b) exhibits tropism for human umbilical cord lymphocytes and bone marrow precursors, but not for human peripheral blood T4 lymphocytes;

(c) is capable of being isolated from human cerebrospinal fluid, but is absent from human peripheral blood T lymphocytes; and (d) does not infect $CD4^+$ continuous lymphoblastoid cell lines. In addition, the retrovirus is in a purified form. The retrovirus can be associated with acute encephalopathy in a patient such that the virus can be isolated from cerebrospinal fluid of the patient. The retroviral variant of the invention can also be in biologically pure form.

This invention also provides a human retrovirus, wherein the retrovirus is a variant of Human Immunodeficiency Virus 1 (HIV-1), and mutants and variants thereof, in a purified form. Isolates and suspensions of the retrovirus in a buffer are provided.

In addition, this invention provides antigen of the human retrovirus of the invention wherein the antigen is in a purified form and is capable of being immunologically recognized by human body fluid containing antibodies to the retrovirus. The antigen can be a protein of the retrovirus, such as a core protein or an envelope protein of the retrovirus.

An immunological complex between antigen of the invention and an antibody recognizing the antigen is also provided. The immunological complex can be labeled with an immunoassay label selected from the group consisting of radioactive, enzymatic, flourescent, chemiluminescent labels and chromophores.

This invention further provides a polypeptide of the human retrovirus of the invention, wherein the polypeptide is in a purified form.

This invention also provides a structural protein of the human retrovirus of the invention in a purified form.

This invention also encompasses a labeled antigen of the human retrovirus of the invention, wherein the antigen is capable of being immunologically recognized by human body fluid containing antibodies to the retrovirus. The antigen can be labeled with an immunoassay label selected from the group consisting of radioactive, enzymatic, fluorescent, chemiluminescent labels and chromophores.

An extract of the human retrovirus is provided, wherein the extract comprises antigen of the retrovirus and the antigen is in purified form and is capable of being immunologically recognized by human body fluid containing antibodies to the retrovirus.

A lysate of the retrovirus is also provided, wherein the lysate comprises antigen of the retrovirus and the antigen is in purified form and is capable of being immunologically recognized by human body fluid containing antibodies to the retrovirus. The lysate can comprise crude lysate of the retrovirus, or it can consist essentially of a lysate of a biologically pure culture of the retrovirus.

A supernatant of a cell culture infected with the retrovirus is provided, wherein the supernatant comprises antigen of the retrovirus and the antigen is capable of being immunologically recognized by human body fluid containing antibodies to the retrovirus. The supernatant can comprise the retrovirus in suspension therein, or the supernatant can be substantially cell-free.

An in vitro diagnostic method for the detection of the presence or absence of antibodies which bind to an antigen of the invention is provided. The method comprises contacting the antigen of the retrovirus of the invention with a biological fluid for a time and under conditions sufficient for the retroviral antigen and antibodies in the biological fluid to form an antigen-antibody complex; and detecting the formation of the complex. The detecting step can further comprise measuring the formation of the antigen-antibody complex. The formation of the antigen-antibody complex is preferably measured by immunoassay based on Western Blot technique or ELISA (Enzyme Linked Immunosorbent Assay) or indirect immunofluorescent assay.

A diagnostic kit for the detection of the presence or absence of antibodies which bind to antigen of the human retrovirus of the invention is also provided. The kit comprises antigens of the retrovirus and means for detecting the formation of immune complex between the antigens and the antibodies. The antigens and the means are present in an amount sufficient to perform the detection.

A specific peptide or purified antigen for example gp 110 (envelope antigen) may account for this specific tropism and then be useful for inhibition of the penetration of the virus in the target cells or to prepare a vaccine against this specific strain prototype of HIV-associated disease.

BRIEF DESCRIPTION OF THE DRAWINGS

This invention will be more fully understood by reference to the drawings in which.

DETAILED DESCRIPTION OF THE PREFERRED EMBODIMENTS

Figure 1:
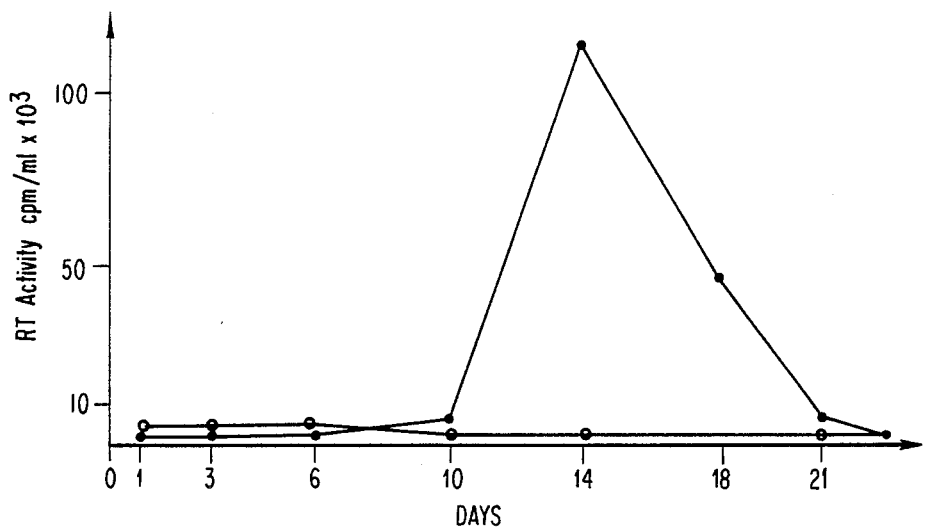
FIG. 1 is a graph in which reverse transcriptase activity in a cell culture of peripheral blood lymphocytes (solid circles) and of cerebrospinal fluid (stars), cocultivated with phytohemagglutin in stimulated peripheral blood cells from a healthy donor, is plotted as a function of time.

Methods for isolating HIV from AIDS and AIDS-Related Complex (ARC) patients and from other donors at risk for these diseases are well known in the art. For example, mononuclear cells prepared from peripheral blood, bone marrow, and other tissues from patients and donors can be stimulated with a mitogen, such as phytohemagglutinin-P, for a period of time. The virus can be established in cell culture using growth medium supplemented with T Cell Growth Factor (TCGF). HIV-1 can usually be isolated from adult peripheral blood of infected patients using this technique. It was surprisingly found, however, that the retroviral variant of the present invention cannot be isolated from human peripheral blood lymphocytes and does not infect normal peripheral blood lymphocytes. Nevertheless, the retroviral variant can be isolated from human cerebrospinal fluid. Thus, while the retroviral variant of the invention is present in human cerebrospinal fluid, HIV-1 would be expected to be found, namely, in peripheral blood lymphocytes.

Once the HIV virus has been isolated, it can be detected using several techniques. One technique involves monitoring supernatant fluids for viral reverse transcriptase activity. Evidence of the retroviral variant of the present invention can be found in human cerebrospinal fluid using this technique; reverse transcriptase activity can be measured in a culture containing the fluid. Conversely, reverse transcriptase activity has not been found in human peripheral blood lymphocytes from the same donor, even though the lymphocytes may originate from a donor testing seropositive for HIV-1.

Another method for identifying HIV involves transmitting the isolated virus to fresh, normal human T lymphocytes, such as umbilical cord blood, adult peripheral blood or bone marrow leukocytes. The known HIV retroviruses usually infect adult peripheral blood lymphocytes, but it has been surprisingly found that the retroviral variant of the invention does not infect human peripheral blood T lymphocytes. Nevertheless, the retrovirus of the invention is capable of infecting human umbilical cord lymphocytes.

HIV in a virus isolate can also be detected by transferring virus to established T cell lines. For example, one neoplastic T-cell line derived from an adult with lymphoid leukemia and termed H9 is known to be susceptible to infection with HIV. In the present case, however, the retroviral variant of the invention does not infect the H9 cell line. Similarly, the retroviral variant of the invention does not infect other CD4+ continuous lymphoblastoid cell lines, such as CEM, which ordinarily are susceptible to HIV-1 infection.

Another method for detectinq HIV in a virus isolate involves testing for antigen expression by indirect immunofluorescence, Western blot procedures, or enzyme linked immunosorbent assay (ELISA) using serum from seropositive donors. Both HIV-1 and the retroviral variant of HIV-1 of the invention are immunologically recognized by human serum containing antibody to HIV-1, even though the serum is from a patient without substantial immunodeficiency or clinical features of lymphadenopathy syndrome, malignancy, or opportunistic infections associated with AIDS, LAS or ARC.

One of the characteristics of the retroviral variant of the invention is that it may be associated with acute encephalopathy in a patient such that the retrovirus can be isolated from cerebrospinal fluid of such a patient. Furthermore, HIV-1 may not be detectable in the patient in either peripheral blood or cerebrospinal fluid after disappearance of encephalopathy, even though the patient is seropositive for antibodies to HIV-1.

This invention will now be more fully described in the following Example.

EXAMPLE

This investigation involves the case of a patient with a positive serology and no sign of AIDS or ARC where the transient isolation of HIV in cerebrospinal fluid was associated with an acute regression encephalitis. This invention suggests that acute expression of HIV in the central nervous system may occur during incubation period and may produce clinical signs and symptoms without immunodeficiency.

More particularly, a 43 year old caucasian homosexual male had been well until midday of May 17, 1986, when he complained of transient vomiting and an unsteady gait which slowly worsened. A week later, he had vomiting again during the day and began to complain of hypersomnia, dysarthria and hicup. He was admitted to the Salpetriere Hospital on June 2nd.

He had been living for one year with a caucasian homosexual male with a positive HIV serology known for eight months. This patient had a primary syphilis on December 1985 treated by penicillin. No HIV serology had been done at that time. HIV serology was conducted for the first time in April 1986 and was positive.

General examination findings were unremarkable, and the patient denied diarrhea, fever, or weight loss. On neurological examination he was awake and fully oriented, but inattentive with poor short term memory and mental slowness. There were a mild dysarthria and gait ataxia as well as volitional movement disorders and astereognosia of the two hands. Cranial nerves, tendon reflexes, optic disk were normal. Electroencephalogram showed discharge of slow waves in left temporal region and few theta rhythm on the right side. A CT scan and nuclear magnetic resonance imaging (0.5 $T_S$ with $T_1$ and $T_2$ weighted sequences) of the brain were considered as normal.

Cerebrospinal fluid contained 5.8 white cells/mm$^3$ with a protein level of 43 mg/dl, and glucose concentration of 93 mg/dl. Cultures and cytology were negative. Study of lymphocytes subpopulation showed CD4+: 44 %; CD8+: 32 %; with a lymphocyte count of 2200/mm$^3$.

Repeated cerebrospinal fluid and blood examinations were made. The results are summarized in Table 1.

TABLE 1

| | | 5/06/86 | 19/08/86 | 20/11/86 | 1/04/87 |
|---|---|---|---|---|---|
| Neurological Symptomatology | | + | − | − | − |
| CSF | Cells/mm$^3$ | 5.8 | 8.2 | 8.6 | 15 |
| | VIRUS | + | − | − | − |
| BLOOD | WBC | 5300/mm$^3$ | 4300/mm$^3$ | 7800/mm$^3$ | 3800/mm$^3$ |
| | Lymphocytes | 42% | 40.3% | 17% | 35.6% |
| | CD4+ | 21% | 43% | 34% | 31% |
| | CD8+ | 32% | 33% | 33% | 23% |
| | VIRUS | − | − | − | ND |
| HIV ANTIBODIES | BLOOD | + | + | + | + |
| | CSF | + | + | + | + |

Legend of Table 1

Virus isolations from PBL and cerebrospinal fluid were attempted according to the method previously described (6). The presence of HIV Antibodies in patient sera and cerebrospinal fluid was assessed both by ELISA and Western Blot analysis. The following symbols have been used in Table 1:

| + | present |
|---|---|
| − | absent |
| ND | not done |
| WBC | white blood cells |
| CSF | cerebrospinal fluid. |

Viral, bacterial and fungal serology remained negative. The patient recovered slowly and spontaneously. Three months later psychometric assessment as well as neurological examination and electroencephalogram were normal.

Antibodies against HIV were detected in sera and cerebrospinal fluid using enzyme linked immunosorbent assay (ELISA) and Western blotting (Elavia and LAV-Blot; Diagnostics Pasteur).

HIV isolation from peripheral blood lymphocytes and cerebrospinal fluid was attempted in June, August, October, and April and was successful only from cerebrospinal fluid collected during June (see Table 1). However, cerebrospinal fluid examination in April 1987 still contained 15 white cells/mm$^3$.

Table 1 also shows that, unlike infection by HIV-1, there was not a marked decrease or depletion of CD4+ cells, nor was there a sharp inversion of CD4+ CD8+ ratio as is generally found in HIV-1 infection.

Virus Isolation and Propagation

Peripheral blood lymphocytes from the patient were cultured or co-cultured with normal peripheral blood lymphocytes (PBL) as previously described (6). All attempts- to isolate HIV from patient peripheral blood lymphocytes were unsuccessful.

Sequential specimens of patient cerebrospinal fluid were co-cultivated with normal peripheral blood lymphocytes previously stimulated with phytohemagglutinin-P (pHA). HIV was isolated only from the culture performed in June (see FIG. 1).

In FIG. 1, 10° patient peripheral blood lymphocytes (PBL) or 1 ml patient cerebrospinal fluid were cocultivated with 3×10$^6$ pHA stimulated PBL from a healthy donor. Virus production in cell free supernatants was followed every 3 or 4 days by measuring reverse transcriptase (RT) activity. The following legend was used in FIG. 1:

| *────* | for cerebrospinal fluid cocultivated with normal PBL, and |
|---|---|
| o────o | for patient lymphocytes cocultivated with normal PBL. |

This isolate was a cytopathic HIV-1 type, but could not be propagated by direct infection of T lymphocytes from a normal donor (FIG. 1), since several assays were negative. The propagation of this isolate was successful only on cord blood lymphocytes (FIG. 2).

Figure 2:
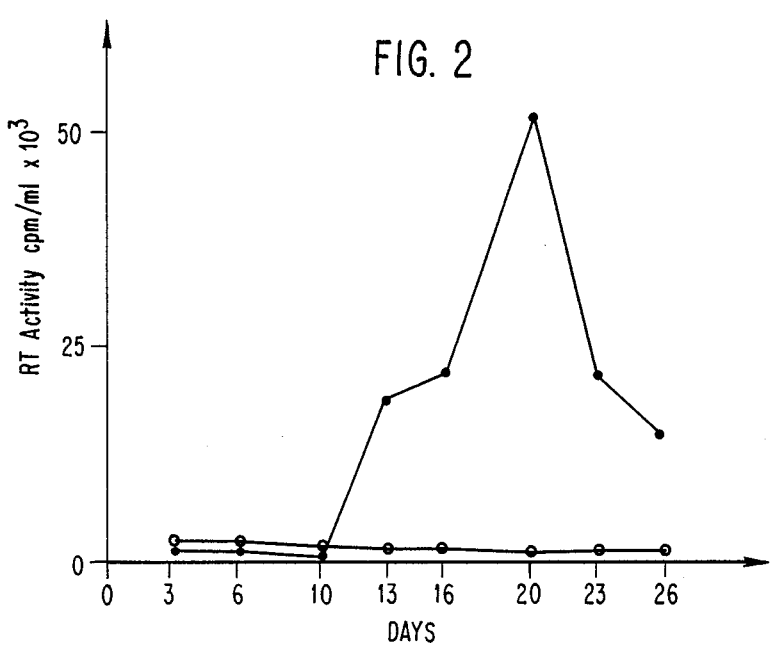
FIG. 2 is a similar graph for cell cultures of peripheral blood lymphocytes (stars) and of cerebrospinal fluid (solid circles) infected with cell-free supernatant of day 14 cell culture of FIG. 1.

In FIG. 2, 10$^6$ cord blood lymphocytes (CBL) were infected with 0.5 ml of 1/10 dilution of cell free supernatant of day 14 cell culture of FIG. 1 or 5000 cpm equivalent reverse transcriptase activity (RT). Supernatants were pelleted each 3–4 days and RT assayed as previously described (6). The following legends are used in FIG. 2:

| | | |
|---|---|---|
| *———* | | for infected PBL, and |
| o———o | | for infected CBL. |

DISCUSSION

The isolate obtained from cerebrospinal fluid could not be directly propagated on peripheral blood lymphocytes from a healthy donor or on CD4+ lymphoblastoid cell lines (CEM or H9). Only cord blood lymphocytes were found to be susceptible to viral infection suggesting that in some asymptomatic carriers the virus might be present in another reservoir than circulating CD4+ lymphocytes. Glial cells are a possible reservoir, and recently an HIV strain from cell free cerebrospinal fluid of a patient dead with Kaposi sarcoma and severe AIDS encephalopathy was able to persist in glial cells (7).

Isolation of HIV-1 from cerebrospinal fluid during the initial course of the disease and the resolution of clinical symptomatology coincident with negative HIV culture from cerebrospinal fluid strongly supports an encephalopathy related to HIV. However, acute expression of HIV may be due to other infections. A recent report showed that herpes simplex virus type 1 (HSV-1) can reactivate transcription of latent HIV in vitro (8). Furthermore, activation of HIV by a transcription factor NF-KB has been demonstrated (9). This factor is produced by activated T lymphocytes. Viral, bacterial or protozoal infection may induce NF-KB production and thus activate virus in dormantly infected cells. Clinical signs or biological data supporting another infection could not be found.

Spontaneous clinical recovery concomitant with disappearance of HIV from cerebrospinal fluid suggests that host defenses are able to control acute expression of the virus, even in the central nervous system. However, the virus is probably still present in the central nervous system of the patient as it is shown by the abnormalities of the cerebrospinal fluid.

Moreover, another lentivirus, Visna Maedi, may produce a progressive or relapsing-remitting leuco-encephalitis in the sheep (10). This invention suggests that reactivation of latent HIV infection in a healthy seropositive patient may produce regressive clinical disabilities. Host defenses are able to control HIV expression.

The retrovirus of the invention (HIV PAR) has been deposited in the Collection Nationale des Cultures de Micro-organismes (CNCM) at Institut Pasteur in Paris, France, on Oct. 29, 1987. Specifically, the retrovirus was deposited under culture collection accession No. CNCM I-710.

While the retrovirus corresponding to CNCM I-710 is specifically described herein, it will be understood that this invention includes within its scope all retroviral mutants and variants thereof. Thus, this invention includes any virus having a similar phenotype or genotype. This invention also includes any virus, viral protein, fragment thereof or peptide having similar patterns of immunological reaction to a retrovirus having the characteristics of CNCM I-710. This invention further includes within its scope all extracts, isolates, lysates, cell supernatants, and cell cultures containing any of these viruses, viral proteins, fragments of the viral proteins or polypeptides corresponding to portions of the proteins.

More particularly, it will be understood that the present invention is intended to encompass the retroviral proteins and peptide fragments thereof in purified form, whether or not glycosylated, and whether obtained using the techniques described herein or other methods. For example, other methods include genetic engineering techniques, such as the expression in a suitable host of a DNA sequence encoding the proteins or polypeptides of the retrovirus. Other methods of course include chemical synthesis of the peptides using conventional organic chemistry techniques.

This invention also includes peptides in which a portion of the retroviral protein containing the antigenic binding site is linked to a larger carrier molecule, such as a polypeptide or a protein, and in which the resulting product exhibits specific binding for antibodies to the retrovirus in vivo or in vitro. In this case, the polypeptide can be smaller or larger than the peptide of the invention.

It will be understood that the peptides of the invention encompass peptides having equivalent peptide sequences. By this it is meant that peptide sequences need not be identical to the sequences of the proteins of the retroviruses of the invention. Variations can be attributable to local mutations involving one or more amino acids not substantially affecting the antibody-bonding capacity of the peptide. Variations can also be attributable to structural modifications that do not substantially affect antibody-binding capacity. Thus, for example, this invention is intended to cover serotypic variants of the proteins and peptides of the invention.

The retroviral proteins, protein fragments and peptides of the present invention can be used to identify antibodies to the retrovirus of the invention in materials and to determine the concentration of the antibodies in those materials. Thus, the proteins, fragments and peptides can be used as antigens for qualitative or quantitative determination of the retrovirus in a material. Such materials of course include biological fluids, such as human body fluids, including human sera. The antigens can be derived, for example, from virus from infected cell cultures or they can be recDNA cloned antigens of the invention. When used as a reagent in an immunoassay for determining the presence or concentration of the antibodies to the retrovirus of the invention, the retroviral antigens of the present invention provide an assay that is convenient, rapid, sensitive, and specific.

Antigens of the invention can be obtained from the retrovirus of the invention by lysis or other suitable processing. For example, the retrovirus can be lysed in the presence of a detergent. Lysis can optionally be carried out in the presence of an agent that inhibits the action of proteases. Separation of the antigens can be carried out using known techniques. For instance, virus in supernatant can be banded on a sucrose gradient, and the antigens can be recovered.

More particularly, the antigens of the invention can be employed for the detection of the retrovirus by means of immunoassays that are well known for use in detecting or quantifying humoral components in fluids. Thus, antigen-antibody interactions can be directly observed or determined by secondary reactions, such as precipitation or agglutination. Thus, radioimmunoprecipitation can be employed. Other immunoassays in which the antigens of the present invention can be employed include, but are not limited to, radioimmunoassay, competition immunoprecipitation assay, enzyme immunoassay, and immunofluorescence assay. It will be understood that tubidimetric, colorimetric and nephelometric techniques can be employed.

Immunoassays can be carried out by immobilizing one of the immunoreagents, either the antigen of the invention or the antibodies to the retrovirus of the invention, on a carrier surface while retaining immunoreactivity of the reagent. The reciprocal immunoreagent can be unlabeled or labeled in such a manner that immunoreactivity is also retained. Typically, an antigen of the invention will be absorbed to beads or microtiter plates. These techniques are especially suitable for use in enzyme immunoassays, such as enzyme linked immunosorbent assay (ELISA). An immunoassay based on Western Blot technique is particularly preferred.

Depending on the use to be made of the retroviral proteins and antigens of the invention, it may be desirable to label the proteins and antigens. Examples of suitable labels are radioactive labels, enzymatic labels, flourescent labels, chemiluminescent labels or chromophores. The methods for labeling retroviral proteins or antigens of the invention do not differ in essence from those widely used for labeling immunoglobulin. The need to label may be avoided by using labeled antibody to the retroviral antigen of the invention or anti-immunoglobulin to the antibodies to the retrovirus as an indirect marker.

The viruses, proteins and antigens of the invention can be purified according to conventional techniques. For example, purification can be carried out by employing differences in molecular weights. Differential migration on a gel or gradient centrifugation can be employed. The antigens according to the invention can be separated from a lysate of the viruses by their affinity for lectins. The lectin can be immobilized on a solid support.

A more thorough purification of the antigens can be performed by immunoprecipitation with the sera of patients known to possess antibodies effective against the antigen, with concentrated antibody preparations, such as polyclonal antibodies, or with monoclonal antibodies directed against the antigen of the invention.

The immunoassay kit of this invention can include a control antigen, such as an antigen prepared from uninfected cells. Use of a control antigen can aid in minimizing the risk of false positions from the assay.

Finally, the invention provides immunogenic polypeptides, and more particularly, protective polypeptides for use in the preparation of vaccine compositions against the retrovirus of the invention. These polypeptides can be produced by chemical synthesis or by genetic engineering techniques. They could be eventually used in combination with specific adjuvants, such as aluminium hydroxide or equivalents, which are alreaady accepted for human use.

In summary, the development of an acute encephalopathy was observed on a healthy Human Immunodeficiency Virus seropositive man while HIV was isolated from cerebrospinal fluid, but not from peripheral blood. Signs and symptoms resolved quickly without treatment. This virus could be propagated only in cord blood lymphocytes, but not in peripheral blood T lymphocytes or in continuous lymphoblastoid cell lines, such as CEM. The absence of virus in patient T lymphocytes or infectivity for T lymphocytes might explain the presence of HIV-associated disease, such as encephalopathy without Immunodeficiency in asymptomatic carrier. Search for Human Immunodeficiency Virus in peripheral blood and cerebrospinal fluid after illness was unsuccessful. This suggests that acute expression of HIV could be controlled by natural host defense and may be reversible despite the fact that the patient remains seropositive. This invention makes it possible to assay for antibodies to the retrovirus of the invention in biological fluids and to prepare immunogenic polypeptides, and more particularly, protective polypeptides for use in the preparation of vaccine compositions against the retrovirus of the invention.

REFERENCES CITED HEREIN

1. CARNE C. A., TEDDER R. S., SMITH A. et al. Acute encephalopathy coincident with seroconversion for anti-HTLV-III. Lancet, 1985, ii, 1206–1208.

2. PETITO C. K., NAVIA B. A., CHO E. S. et al. Vacuolar myelopathy pathologically resembling subacute combined degeneration in patient wit the acquired immunodeficiency syndrome. N. Eng. J. Med., 1985, 312: 874–879.

3. NAVIA B. A., CHO E. S., PETITO C. K. et al. The AIDS dementia comples: II. Neuropathology. Ann. Neurol., 1986, 19: 525–535.

4. NAVIA B. A., PRICE R. W. The AIDS dementia complex as the presenting or sole manifestation of human immunodeficiency virus infection. Arch. Neurol., 1987, 44: 65–69.

5. HO D. D., ROTA T. R., SCHOOLEY R. T. et al. Isolation of HTLV-III from cerebrospinal fluid and neural tissues of patients with neurological syndrome related to the acquired immunodeficiency syndrome. N. Eng. J. Med., 1985, 313: 1493–1497.

6. BARRE-SINOUSSI F., CHERMANN J-C., REY F. et al. Isolation of a T lymphotropic retrovirus from a patient at risk for acquired immunodeficiency syndrome (AIDS). Science, 1983, 220: 868–871.

7. KOYANNAGI Y., MILES S., MITSUYASU R. T. et al. Dual infection of the central nervous system by AIDS virus with distinct cellular tropism. Science, 1987, 236: 819–822.

8. MOSCA J. D., BEDNARIK D. P., RAJ N. B. K. et al. Herpes simplex virus type-1 can reactivate transcription of latent human immunodeficiency virus. Nature, 1987, 325: 67–70.

9. NABEL G., BALTIMORE D. An inductible transcription factor activates expression of human immunodeficiency virus in T cells. Nature, 1987, 326: 711–713.

10. JOHNSON R. T. Viral infections of the nervous system. New York: Raven Press, 1982, 239–241.

What is claimed is:

1. A substantially pure preparation of a retrovirus strain deposited under culture collection accession number CNCM I-170.

* * * * *